(12) United States Patent
Cottrell et al.

(10) Patent No.: US 9,255,046 B2
(45) Date of Patent: *Feb. 9, 2016

(54) MANUFACTURING PROCESS FOR HFO-1234ZE

(75) Inventors: Stephen A. Cottrell, Baton Rouge, LA (US); Hsueh Sung Tung, Getzville, NY (US); Haiyou Wang, Amherst, NY (US); Yuon Chiu, Denville, NJ (US); Gustavo Cerri, Parsippany, NJ (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 1214 days.

This patent is subject to a terminal disclaimer.

(21) Appl. No.: 12/125,045

(22) Filed: May 21, 2008

(65) Prior Publication Data

US 2010/0022809 A1    Jan. 28, 2010

Related U.S. Application Data

(63) Continuation-in-part of application No. 11/592,442, filed on Nov. 3, 2006, now Pat. No. 7,880,040, and a continuation-in-part of application No. 11/588,466, filed on Oct. 27, 2006, now Pat. No. 7,563,936, and a continuation-in-part of application No. 10/694,272, filed on Oct. 27, 2003, now Pat. No. 7,230,146, and a continuation-in-part of application No. 10/626,997, filed on Jul. 25, 2003, now Pat. No. 7,592,494.

(60) Provisional application No. 60/939,582, filed on May 22, 2007.

(51) Int. Cl.
| | |
|---|---|
| *C07C 17/00* | (2006.01) |
| *C07C 19/08* | (2006.01) |
| *C07C 21/18* | (2006.01) |
| *C07C 23/00* | (2006.01) |
| *C07C 25/13* | (2006.01) |
| *C07C 17/25* | (2006.01) |
| *C07C 17/358* | (2006.01) |

(52) U.S. Cl.
CPC .............. *C07C 17/25* (2013.01); *C07C 17/358* (2013.01)

(58) Field of Classification Search
None
See application file for complete search history.

(56) References Cited

U.S. PATENT DOCUMENTS

| | | | |
|---|---|---|---|
| 2,889,379 A | 6/1959 | Ruh et al. | |
| 3,472,826 A | 10/1969 | Potts et al. | |

(Continued)

FOREIGN PATENT DOCUMENTS

| | | |
|---|---|---|
| EP | 0522693 | 1/1993 |
| EP | 0974571 | 1/2000 |

(Continued)

OTHER PUBLICATIONS

Dunning, H. Ind. Eng. Chem., 1953, 45(3), 551-564.*

(Continued)

*Primary Examiner* — Clinton Brooks
(74) *Attorney, Agent, or Firm* — Bruce Bradford

(57) ABSTRACT

Disclosed is a method for forming HFO-1234ze, and for forming compositions comprising HFO-1234ze, by (a) converting, preferably by dehydrofluorination, pentafluoropropane (HFC-245), preferably 1,1,1,3,3-pentafluoropropane (HFC-245fa), preferably by contact with a caustic solution, to a reaction product comprising cis-HFO-1234ze and trans-HFO-1234ze; and (b) contacting at least a portion, preferably substantially portion, and in certain embodiments substantially all of said reaction product with at least one isomerization catalyst to convert at least a portion, and preferably at least a substantial portion, of cis-HFO-1234ze in said reaction product to trans-HFO-1234ze.

19 Claims, 1 Drawing Sheet

HFO-1234ze Process

(56) References Cited

U.S. PATENT DOCUMENTS

| | | | |
|---|---|---|---|
| 2,996,555 | A | 8/1972 | Rausch et al. |
| 4,465,786 | A | 8/1984 | Zimmer et al. |
| 4,650,914 | A | 3/1987 | Woodard |
| 4,798,818 | A | 1/1989 | Baizer et al. |
| 4,900,874 | A | 2/1990 | Ihara et al. |
| 5,155,082 | A | 10/1992 | Tung et al. |
| 5,532,419 | A | 7/1996 | Van Der Puy et al. |
| 5,545,777 | A | 8/1996 | Morikawa et al. |
| 5,574,192 | A | 11/1996 | Van Der Puy et al. |
| 5,679,875 | A | 10/1997 | Aoyama et al. |
| 5,710,352 | A | 1/1998 | Tung |
| 5,728,904 | A | 3/1998 | Van Der Puy et al. |
| 5,895,825 | A | 4/1999 | Elsheikh et al. |
| 5,969,198 | A | 10/1999 | Thenappan et al. |
| 5,986,151 | A | 11/1999 | Van Der Puy |
| 6,023,004 | A | 2/2000 | Thenappan et al. |
| 6,031,141 | A | 2/2000 | Mallikarjuna et al. |
| 6,111,150 | A | 8/2000 | Sakyu et al. |
| 6,124,510 | A | 9/2000 | Elsheikh et al. |
| 6,369,284 | B1 | 4/2002 | Nappa et al. |
| 6,472,573 | B1 | 10/2002 | Yamamoto et al. |
| 6,548,719 | B1 | 4/2003 | Nair et al. |
| 6,809,226 | B1 | 10/2004 | Pennetreau et al. |
| 6,958,424 | B1 | 10/2005 | Nair et al. |
| 7,420,094 | B2 * | 9/2008 | Petrov et al. ........... 570/151 |
| 7,485,760 | B2 * | 2/2009 | Wang et al. ........... 570/236 |
| 7,638,660 | B2 * | 12/2009 | Wang et al. ........... 570/236 |
| 2003/0060670 | A1 | 3/2003 | Van Der Puy et al. |
| 2005/0020862 | A1 * | 1/2005 | Tung et al. ........... 570/164 |
| 2005/0090698 | A1 | 4/2005 | Merkel et al. |
| 2005/0171391 | A1 | 8/2005 | Janssens et al. |

FOREIGN PATENT DOCUMENTS

| | | |
|---|---|---|
| EP | 0644173 | 9/2007 |
| EP | 1900716 A | 3/2008 |
| EP | 1918269 A | 5/2008 |
| JP | 11-140002 A | 5/1999 |
| JP | 2000169404 | 6/2000 |
| WO | 9504021 | 2/1995 |
| WO | 9601797 | 1/1996 |
| WO | 9821171 | 5/1998 |
| WO | 9833755 | 8/1998 |
| WO | 03027051 | 4/2003 |
| WO | 2005012212 | 2/2005 |
| WO | 2005108332 | 11/2005 |

OTHER PUBLICATIONS

Burton D J et al: "Preparation of E-1,2,3,3,3-Pentafluoropropene, Z-1, 2,3,3,3-Pentafluoropropene and E-1-Iodopentafluoropropene" Journal of Fluorine Chemistry, Elsevier, NL vol. 44, No. 1, Jul. 1, 1989, pp. 167-174, XP000008378; ISSN: 0022-1139, p. 169.

Corresponding—First Office Action in Japanese Application No. 2010-509545, dated Mar. 1, 2013.

Knunyants I. L. et al.: "Reactions of Fluoro Olefins Communication 13, Catalytic Hydrogenation of Perfluoro Olefins" Bulletin of Academy of Sciences of the USSR, Division of Chemical Sciences, 1960, pp. 1312-1317, XP000578879; ISSN: 0568-5230, p. 1313, (XI)->(XIII) p. 1316, paragraph 6.

Henne, et al., Fluorinated Derivatives of Propane and Polypylene VI, Journal of American Chemical Society, 68-496-497 (1946).

Free-radical additions to unsaturated systems, Journal of Chemical Society, Section C: Organic, (3), 414-21, p. 415, 1970.

Terrant, et al., Free Radical Additions Involving Fluorine Compounds. IV. The addition of Dibromodifluoromethane to some fluoroolefins, Journal of American Medical Society, 77,2783-2786 (1955).

* cited by examiner

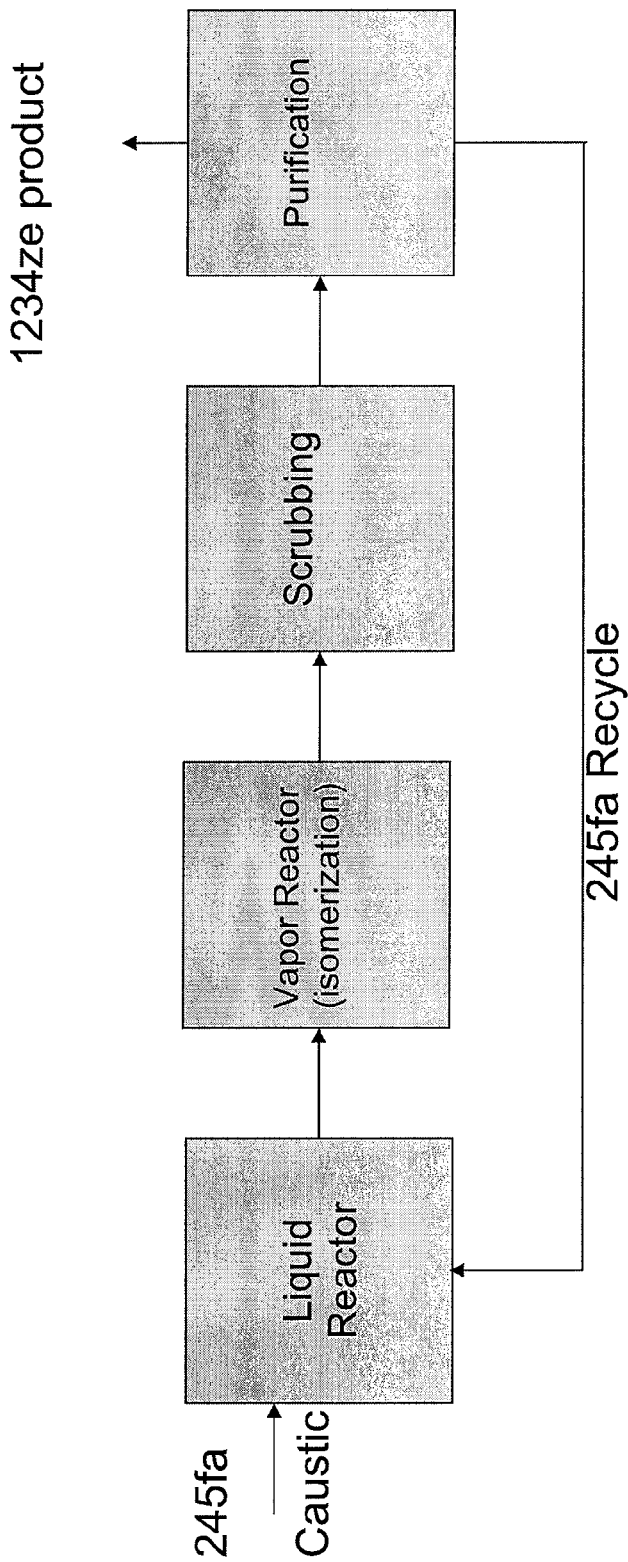

MANUFACTURING PROCESS FOR HFO-1234ZE

CROSS-REFERENCES TO RELATED APPLICATIONS

This application relates to and claims the priority benefit of provisional application 60939582, filed May, 22, 2007. This application is also a continuation in part and claims the priority benefit of the following pending U.S. application Ser. No. 11/592,442, filed Nov. 6, 2006; Ser. No. 11/588,466, filed Oct. 27, 2006; Ser. No. 10/694,272, filed Oct. 27, 2003; and Ser. No. 10/626,997, filed Jul. 25, 2003. Each of the above noted regular applications and the provisional application are incorporated herein by reference. Also incorporated herein by reference, in its entirety, is U.S. Pat. No. 5,986,151.

BACKGROUND OF INVENTION

(1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such tetrafluoropropenes, including particularly 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing HFO-1234ze are known. For example, U.S. Pat. No. 6,124,510 discloses a process for preparing a product stream containing HFO-1234ze. The described process comprises the step of dehydrofluorination of HFC-245fa using either an alkaline solution of a strong base (such as an aqueous or alcoholic solution of potassium hydroxide), or a chromium-based catalyst, preferably in a vapor phase. The composition produced by the examples of the disclosed processes contains relatively large concentrations of the cis-isomer of HFO-1234ze. More specifically, the three examples disclosed in this patent produce compositions containing both trans-HFO-1234ze and cis-HFO-1234ze, with amount of cis-isomer in the composition ranging from 17.7% to 23.9%. As a result, the methods disclosed in U.S. Pat. No. 6,124,510, as described in the examples thereof, produce product compositions having a relatively low concentration of trans-HFO-1234ze, namely, concentrations ranging from 74% to 80.5%.

Applicants have come to appreciate the need for and have developed processes for producing, preferably in an efficient and cost effective manner, compositions containing HFO-1234ze having relatively high concentrations of trans-isomer. In one aspect, applicants have determined that known processes are generally not economical relative to their product yield, particularly due to the formation of significant amounts of the undesired cis-isomer in the product stream of such know processes.

BRIEF DESCRIPTION OF THE DRAWING

FIG. 1 is a block flow diagram showing in schematic form one embodiment of the present invention.

SUMMARY OF THE INVENTION

Applicants have developed methods for preparing compositions comprising fluorinated organic compounds, including particularly HFO-1234ze, in which the percentage trans-HFO-1234ze is relatively high, more preferably at least about 85%, more preferably at least about 90%, and even more preferably at least about 95% based on the total weight of HFO-1234ze in the composition.

Another aspect of the present invention relates to a process for forming trans-HFC-1234ze which is economical on a commercial scale, and preferably more economical than prior art processes, and/or which preferably produces trans-HFO-1234ze at a relatively high yield, preferably at a yield which is higher than the yield of commercial processes of the type heretofore known.

In preferred embodiments, the present invention provides a method for forming HFO-1234ze, and for forming compositions comprising HFO-1234ze, by (a) converting, preferably by dehydrofluorination, pentafluorpropane (HFC-245), preferably 1,1,1,3,3-pentafluorpropane (HFC-245fa), preferably by contact with a caustic solution, to a reaction product comprising cis-HFO-1234ze and trans-HFO-1234ze; and (b) contacting at least a portion, preferably substantially portion, and in certain embodiments substantially all of said reaction product with at least one isomerization catalyst to convert at least a portion, and preferably at least a substantial portion, of cis-HFO-1234ze in said reaction product to trans-HFO-1234ze. In preferred embodiments, the said contacting step (b) comprises providing said reaction product from step (a) in the form of a vapor phase and contacting said vapor phase reaction product with a metal-based catalyst, preferably a metal-base catalyst in solid form, and even more preferably a metal-based catalyst comprising fluorine. In certain preferred embodiments, the metal-based catalysts comprises chrome (including all of its ionization states). In certain preferred embodiments, the metal-based catalysts comprises aluminum (including all of its ionization states).

DETAILED DESCRIPTION OF PREFERRED EMBODIMENTS

One beneficial aspect of the present invention is that it enables the production of desirable fluoroolefins, preferably C3 fluoroolefins, using relatively high conversion and high selectivity reactions. Furthermore, the present methods in certain preferred embodiments permit the production of the desirable fluoroolefins from relatively attractive starting materials. For example, pentafluoropropene, particularly 1,1,3,3,3-pentafluoropropane (HFC-245fa) may in certain embodiments be an advantageous starting material. This compound is generally considered relatively easy to handle, and it is generally readily available in commercial quantities or can be easily produced from other readily available materials.

Preferably HFC-245fa is exposed in a first converting step to reaction conditions effective to produce a reaction product containing both cis- and trans-HFO-1234ze. In one preferred aspect of the present invention, the converting step (a) comprises exposing HFC-245fa to reaction conditions that are sometimes referred to herein for convenience, but not necessarily by way of limitation, as a dehydrohalogenation reaction or more particularly in certain embodiments as a dehydrofluorination reaction. In preferred embodiments, at least a portion of the reaction product from the first converting step (a), and preferably substantially all of the reaction product from the first converting step (a), is exposed in a second converting step (b) to reaction conditions effective to selectively convert the cis-HFO-1234ze to trans-HFO-1234ze. According to certain preferred aspects of the invention, this second converting step (b) comprises exposing at least a portion of the reaction product from converting step (a) to reaction conditions that are sometimes referred to herein for convenience, but not necessarily by way of limitation, as an isomerization reaction. Certain preferred embodiments of the invention are described below, with the headings being used for convenience but not necessarily by way of limitation.

I. Dehydrofluorination

In certain preferred embodiments, the converting step (a) is carried out under conditions effective to provide a HFC-245, and more preferably a HFC-245fa conversion of at least about 40%, more preferably at least about 55%, and even more preferably at least about 70%. In certain preferred embodiments the conversion is at least about 90%, and more preferably about 100%. Further in certain preferred embodiments, the HFC-245 (and preferably HFC-245fa) is converted in conversion step (a) under conditions effective to provide a selectivity to HFO-1234ze of at least about 85%, more preferably at least about 90%, and more preferably at least about 95%, and even more preferably about 100%.

The preferred converting step (a) comprises a liquid phase reaction, although in certain embodiments it may comprise a gas phase or a combination of gas and liquid phase reactions, and it is contemplated that the reaction can be carried out batch wise, continuous, or a combination of these. Examples of other reaction mechanisms that may be used for the converting step (a) are described in U.S. application Ser. No. 11/592,442, which was published as US 2007/0129580.

One preferred converting step involves a reaction in which HFC-245fa is contacted with a dehydrohalogenating agent, such as potassium hydroxide (KOH), sodium hydroxid (NaOH), Ca(OH)$_2$, CaO, and combinations of these and/or other catalysts, to form a reaction product comprising both cis- and tran-HFO-1234ze. This reaction may be described, by way of illustration but not necessarily by way of limitation, by the following reaction equation:

In preferred aspects of such embodiments, the dehydrohalogenating agent comprises, and in certain embodiments consists essentially of, caustic material, such as KOH, and is preferably provided as an aqueous solution comprising from about 2% to about 100%, more preferably from about 5% to about 90%, and even more preferably from about 10% to about 80% by weight of the caustic material, preferably comprising or consisting essentially of KOH.

In certain preferred embodiments, the caustic solution, and preferably the KOH solution, is brought to a temperature of from about 20° C. to about 100° C., more preferably from about 30° C. to about 90° C., and most preferably from about 40° C. to about 80° C. The reaction pressure in such embodiments may vary, depending on particular processing parameters of each application. In certain embodiments, the reaction pressure ranges from atmospheric pressure, superatmospheric pressure or under vacuum. The vacuum pressure, when used, preferably in certain embodiments ranges from about 5 torr to about 760 torr.

B. Isomerization

The reaction product from step (a) may be undergo intermediate processing before introduction to the isomerization reaction, although it is contemplated that such intermediate steps may be eliminated. In one preferred embodiment, the reaction product from the conversion step (a) is first dried, for example with a desiccant such as molecular sieve or sulfuric acid, and is fed into an isomerization reactor which is operated under conditions to selectively convert the cis-form of the fluorinated olefin to the tran-form of the same olefin. In preferred embodiments, the reaction is carried out in the presence of a catalyst. In preferred embodiments, suitable isomerization catalyst include fluorinated chromia, chromium fluoride, fluorinated alumina, aluminum fluoride, etc., and the reaction is carried out under conditions to convert a portion, preferably a substantial portion, and most preferably substantially all of the cis-form, preferably cisHFO-1234ze, into transHFO-1234ze. In certain embodiments, the reaction is carried out under conditions effective to convert at least about 50 percent, and even more preferably at least about 70 percent, of the cis-form compound to the trans-form compound. One important element of such preferred embodiments derives from the discovery by applicants that certain catalysts, when employed in accordance with the teachings contained herein, are capable of effectively achieving such high conversion and selectivity levels for such reactions.

It is contemplated that a wide cis-concentrations may be present in the process streams which is fed to the isomerization reaction. For example, in certain embodiments of the present invention the isomerization feed stream which contains the cis-form of the compound to be converted may contain relatively low concentrations of this compound, for example less than about 50% by weight, or perhaps is even as little as 1% by weight. Generally, however, it is more preferred in many embodiments that the feed stream containing the cis-form of the compound to be converted in accordance with the present invention contains relatively high concentrations of the cis-molecule. Thus, in preferred embodiments, the feed stream in accordance with the preferred aspects of the present invention comprises at least about 5% by weight of the cis-form of the molecule, more preferably at least about 7% by weight, and even more preferably at least about 10% by weight of the cis-form of the molecule. Such high concentrations of the cis-molecule may be achieved in certain embodiments, for example, by exposing the crude reaction product stream from the converting step (a) to fractional distillation (or other separation processes) so as to create a stream relatively concentrated in the cis-form of the molecule (and perhaps unreacted HFC-245).

One aspect of preferred embodiments of the present invention includes converting the cis-form of fluorinated olefin in such a stream and/or other similar streams which have been processed (by separation, for example) from converting step (b) reaction product stream(s) to the trans-form, preferably at a conversion of at least about 1 percent, more preferably at least around 70%, and even more preferably at least about 90%, while at the same time preferably achieving a selectivity to the trans-form of the compound that is at least about 80%, even more preferably at least about 95%, and in certain highly preferred embodiments at least about 98%.

It is contemplated that the isomerization step may be preformed using a wide variety of process parameters and process conditions in view of the overall teachings contained herein, such as for example it is contemplated that the isomerization step may comprise, in certain nonpreferred embodiments, a liquid phase reaction. However, it is preferred in many embodiments of the present invention that this reaction step comprise a gas phase reaction, preferably in the presence of catalyst, preferably a metal catalyst.

Applicants have found that such highly desirable levels of cis- to trans-conversion and selectivity, and particularly and preferably from feed streams as described herein, by the proper selection of operating parameters, including, but not necessarily limited to, catalyst type, reaction temperature, and reaction residence time. Preferred aspects of each of these parameters are described below.

Applicants have found that three general types of catalysts are highly desirable and effective, when used in accordance with teachings contained herein, to achieve the aforesaid high level of conversion and selectivity. More specifically, preferred embodiments of the present processes generally comprise exposing the cis-form of the compound to a metal based catalyst selected from the group consisting of halogentated metal oxides, Lewis acid metal halides, zero-valent metals, and combinations of these.

With respect to catalysts comprising halogenated metal oxides and/or Lewis Acid metal halides, it is preferred that the metal component comprises, and preferably consists essentially of, one or more metals selected from transition metals, Boron group metals, rare earth metals, group VA metals, alkali metals, alkali earth metals, and combinations of these.

Although it is contemplated that many transition metals may be adaptable for use as the metal component in the catalysts of the present invention, it is generally preferred in certain embodiments that the catalyst include a transition metal component selected from the group consisting of transition metals with an atomic number from about 21 to about 57 and transition metals having an atomic number of 77 (iridium) or 78 (platinum). For catalysts which have a metal component selected from the Boron group, such metals having an atomic number of from about 13 to about 81 are preferred, with Tl and Al being preferred from among these. For catalysts which have a metal component selected from the alkali earth metals, Mg is preferred. For catalysts which have a metal component selected from the Group VA metals, Sb is preferred. (As used herein, references to the Periodic Table are to the Periodic Table of The Elements—CAS version, unless specifically indicated otherwise). For catalysts which have a metal component selected from among the alkali metals, those metals having an atomic number of from about 3 to about 37 are preferred, with those having an atomic number of from about 3 to about 19 being even more preferred. For catalysts which have a metal component selected from the rare earth metals, cerium is preferred. Of course it is contemplated that any and all combinations of the above-noted metal components, and other metal components not mentioned here, may be used in combination in accordance with the present invention.

For catalysts which are halogenated metal oxide catalysts (which are sometimes referred to herein for convenience as HMO catalysts) and Lewis Acid catalysts (which are sometimes referred to herein for convenience as LA catalysts), it is generally preferred that the catalysts include a transition metal or Al, and preferably when a transition metal is present it is selected from the group consisting of transition metals with an atomic number from about 21 to about 57, and combinations of these. From among the transition metals for use in HMO and LA catalysts, metals from Group VIB are preferred in certain embodiments, with Cr being especially preferred from among this group. In general for HMO and LA catalysts which include a transition metal component, the metal is preferably selected from the group consisting of Cr, Mo, V, Nb, Fe, La, Ni, Zn and combinations of these. In general for HMO and LA catalysts which include rare earth metal component, the metal is preferably Ce. In general for HMO and LA catalysts which include boron metal component, the metal is preferably selected from Al, Tl, and combinations of these. In general for HMO and LA catalysts which include an alkali earth metal component, the metal is preferably Mg. In general for HMO and LA catalysts which include alkali metal components, the metal is preferably selected from Li, Na, K and combinations of these.

It is contemplated that the metals used in the HMO catalysts and the LA catalysts of the present invention can be used in any available oxidation state. It is preferred in certain embodiments that the metals are used in accordance with the following oxidations states:

$Cr^{3+}$ and $Cr^{6+}$
$Mo^{6+}$
$V^{5+}$
$Nb^{5+}$
$Sb^{5+}$
$Ti^{4+}$
$Zr^{4+}$
$Ce^{4+}$
$Al^{3+}$
$Fe^{3+}$
$La^{3+}$
$Mg^{2+}$
$Ni^{2+}$
$Zn^{2+}$
$Li^{+}$
$Na^{+}$
$K^{+}$ In general, any halogen can be used as the component that is included in the HMO of the present invention. It is preferred, however, that the HMO catalyst of the present invention comprises a fluorinated metal oxide, more preferably a fluorinated transition metal oxide, and even more preferably fluorinated transition metal oxide wherein the metal is selected from the group consisting of Cr, Mo, V, Nb, Fe, La, Ni, Zn and combinations of these, fluorinated chromium oxide being highly preferred in certain embodiments. The agent and conditions used to treat the metal oxide to form the HMO catalyst can vary widely within the scope of the present invention. It is preferred in certain embodiments that the metal oxide be treated with one or more of the following halogenating agents: HF, F2, HCl, Cl2, HBr, Br2, HI, I2 and combinations of these. In certain highly preferred embodiments, the halogenating agent comprises one or more of HF, F2, HCl, Cl2, HBr, Br2, and combinations of these, and even more preferably HF, F2, HCl, Cl2F and combinations of these, and even more preferably HF, F2, and combinations of these.

In general, any coordinating component can be used as the component that is included in the LA of the present invention. It is preferred, however, that the LA catalyst of the present invention comprises a Lewis Acid halide, more preferably a Lewis Acid halide in which the halogen component is selected from F, Cl, Br, I and combinations of these, more preferably F, Cl, Br and combinations of these, even more preferably F, Cl and combinations of these, and most preferably F. In certain highly preferred embodiments, the Lewis Acid catalyst is a Lewis Acid halide, preferably a fluoride, formed from a transition metal, and even more preferably a Lewis Acid halide formed from a transition metal selected from the group consisting of Cr, Mo, V, Nb, Fe, La, Ni, Zn and combinations of these, with Cr and Fe being preferred in certain embodiments. The agent and conditions used to form the LA catalyst can vary widely within the scope of the present invention. It is preferred in certain embodiments that the LA catalyst be formed, for example, by dissolving in an aqueous halogen salt, followed by evaporation and calcination. In one particular, but not limiting example, the process of forming the catalyst comprises: 1) dissolving quantities of metal hydroxides, oxides, and/or carbonates preferably, in aqueous HF solution (preferably separately in 49% aqueous HF solution), with mixing in a Teflon® container; 2) evaporation of the solution to dryness; 3) calcining the dried sample at an elevated temperature for a sufficiently long period, preferably in the presence of inert gas, such as N2; and 4) optionally but preferably forming particles of the material so produced, preferably by grinding, to a fine powder, and then preferably by pelletizing into desired shapes.

With respect to neutral metal catalysts (which are sometimes referred to herein for convenience as NM catalysts), it is generally preferred that the catalysts include one or more transition metals selected from groups VIII and IB, with Co and Pd being preferred in certain embodiments.

The particular form of the catalyst can also vary widely. For example, the catalysts of this invention may contain other components, some of which may be considered to improve the activity and/or longevity of the catalyst composition. Preferred catalysts may in certain embodiments be promoted with compounds of molybdenum, vanadium, tungsten, silver, iron, potassium, cesium, rubidium, barium or combinations thereof. The catalyst may contain other additives such as binders and lubricants to help insure the physical integrity of the catalyst during granulating or shaping the catalyst into the desired form. Suitable additives include magnesium stearate, carbon and graphite. When binders and/or lubricants are added to the catalyst, they normally comprise about 0.1 to 5 weight percent of the weight of the catalyst. Furthermore, the catalyst may be used in a form where it is either unsupported or supported on a substrate, or in some cases a combination of these forms. It is contemplated that all types of supports known to those skilled in the art are useful in accordance with the present invention. By way of example, any of the catalysts mentioned herein may be supported on one or more materials, including but necessarily limited to the following: carbon; activated carbon; graphite; silica; alumina; fluorinated graphite; fluorinated alumina; and combinations of any two or more of these.

The catalyst may be activated prior to use by either HF treatment for HMO and LA catalysts or H2 treatment for NM catalysts at elevated temperatures. After use for a period of time in the process of this invention, the activity of the catalyst may decrease. When this occurs, the catalyst may be reactivated. Reactivation of the catalyst may be accomplished by any means known in the art, for example, by passing air or oxygen diluted with nitrogen over the catalyst at temperatures of from about 100° C. to about 400° C., preferably from about 200° C. to about 375° C., for from about 0.5 hour to about 3 days, followed by either HF treatment at temperatures of from about 25° C. to about 400° C., preferably from about 200° C. to about 350° C., for HMO and LA catalysts or H2 treatment at temperatures of from about 100° C. to about 400° C., preferably from about 200° C. to about 350° C., for NM catalysts.

It is also contemplated that the present processes, in view of the overall teachings contained herein, may be adaptable for use in accordance with a wide variety of reaction temperature conditions. For example it is contemplated that the reaction temperature in preferred embodiments may be from about 10° C. to about 600° C. As used herein, the term "reaction temperature" refers to the average temperature in the catalyst bed, unless otherwise indicated herein. In many embodiment, the isomerization is preferably conducted at temperatures ranging from about 20° C. to about 500° C., more preferably from about 50° C. to about 200° C. In certain preferred embodiments, the reaction temperature is from about 20° C. to about 100° C., more preferably for about 30° C. to about 90° C. and even more preferably for about 40° C. to about 80° C.

While it is contemplated that these preferred ranges have application generally to conversion reactions in accordance with the present invention, such ranges produce in certain embodiments especially exceptional results, for example in connection with an isomerization of 1,1,1,3-tetrafluorpropenes. It is also contemplated that a wide variety of pressures may be used in connection with the processes of the present invention. Nevertheless, in certain preferred embodiments, the reaction is carried out under pressure conditions ranging from a vacuum of about 5 torr to about 200 psig.

It is also contemplated that a wide variety of contact times for the preferred reactions of the present invention may be used. Nevertheless, in certain preferred embodiments, the residence time is preferably from about 0.5 sec to about 600 sec.

In preferred aspects of the present invention, the cis-form of the compound to be converted is contained in a feed stream, and the converting step includes providing one or more reaction vessels, at least one of which preferably contains catalyst of the present invention and introducing the feed stream into the vessel(s) under conditions effective to achieve the desired conversion. It should be appreciated that the term "stream" as used herein is not limited to the singular, and it is contemplated that in certain embodiments separate streams be combined outside the vessel and then introduced to the vessel together, or in other embodiments separate streams might constitute the reactor feed, each of which is introduced into the vessel(s) at different times and/or at different locations. This same convention has been used and applied herein throughout to all use of the term "stream" herein, unless specifically indicated otherwise.

Thus, in preferred embodiments the conditions effective to achieve the desired high levels of conversion and selectivity include exposing the feed to a metal based catalyst selected from the group consisting of halogentated metal oxides, Lewis acid metal halides, zero-valent metals, and combinations of these, preferably under reaction conditions, including reaction temperature and residence time, effective to convert at least about 5% of the cis-form of the compound to other compounds and to further achieve a selectivity to the trans-form of the compound of at least about 70%.

The reaction pressure may vary, but in certain embodiments, the pressure preferably is from about a vacuum to about 300 psi. In certain preferred embodiments, atmospheric pressure is used. In many such preferred embodiments, the effluent from the isomerization reactor is preferably fed to a distillation train where transHFC-1234ze is purified to product specification and unreacted HFC-245fa and cisHFC-1234ze is separated and may be recycled to reaction step (a) or reaction (b), or both. By-products of the reaction are separated and disposed of appropriately.

It should be understood, that the order of the purification steps may be modified such that HFC-1234ze (trans) is isolated by distillation after step (a) and unreacted HFC-245fa and HFC-1234ze (cis) are fed to the reactor of step (b). The product HFC-1234ze (trans) from the reactor of step (b) may then be purified by distillation.

EXAMPLES

Additional features of the present invention are provided in the following examples, which should not be construed as limiting the claims in any way.

Example 1

HFC-245fa Dehydrofluorinaton Using Caustic Solution

About 1673 pounds of HFC-245fa was fed into a reaction vessel containing a 20% molar excess of 45% KOH. A small amount of a phase transfer catalyst, Aliquat 336 was added to aid the reaction. The reaction was conducted at a temperature of 60 C and the pressure was allowed to increase to greater than 150 psig and the product was taken. Analysis of the product showed a 95.1% conversion of the HFC-245fa and a selectivity of 86.9% to HFC-1234ze (trans) and 13.1% to HFC-1234ze (cis).

Example 2

Isomerization of cis-1234ze Over Selected Catalysts

Three different kinds of catalysts, namely, fluorinated metal oxide, metal fluoride(s), and supported metal, were used for cis-1234ze isomerization in Example 2. In each case, 20 cc of catalyst was used. A mixture of 85.3% cis-1234ze/14.7%245fa was flowed over catalyst at a rate of 12 g/h. For a specified catalyst, a suitable reaction temperature was carefully chosen such that almost no dehydrofluorination reaction occurs to the HFC-245fa included in the feed. As shown in Table 2, all the catalysts except about 0.5 wt % Co/AC listed in Table 2 provided a high activity (>80% cisHFO-1234ze conversion) and a high selectivity to transHFO-1234ze (>95%) during cisHFO-1234ze isomerization. The 0.5 wt % Co/AC catalyst exhibited a moderate activity (45% of cis-1234ze conversion) and a high selectivity to trans-1234ze (about 98%).

TABLE 2

Isomerization of cis-1234ze over various catalysts

| Catalyst | Reaction temp. (C.) | conversion, % cis-1234ze | selectivity, % trans-1 234ze |
|---|---|---|---|
| Fluorinated $Cr_2O_3$ | 100 | 91.0 | 100.0 |
| $AlF_3$ | 200 | 85.2 | 99.3 |
| $FeF_3$ | 300 | 80.9 | 100.0 |
| 0.5 wt % Co/AC | 350 | 45.0 | 98.2 |

Reaction conditions: 20 cc catal., 12 g/h 85.3%, cis-1234ze/14.7% 245fa, 1 atm

What is claimed is:

1. A process for the manufacture of a composition comprising trans-1,3,3,3 tetrafluoropropene (transHFO-1234ze) comprising:
   a) converting 1,1,1,3,3-pentafluoropropane to a reaction product comprising cis-1,3,3,3 tetrafluoropropene (cis-HFO-1234ze) and trans-HFO-1234ze;
   b) producing a feed stream comprising at least a portion of said cis-HFO-1234ze and said trans-HFO-1234ze from the reaction product of said converting step (a), wherein the amount of cis-HFO-1234ze in said feed stream is at least about 5% based on the total of HFO-1234ze in said feed stream;
   c) introducing said feed stream to an isomerization reactor having catalytic reaction conditions effective to convert at least about 70% of said cis-1,3,3,3 tetrafluoropropene in said feed stream, said conditions comprising exposing at least a portion of said cis-1,3,3,3 tetrafluoropropene in said feed stream to a metal based catalyst selected from the group consisting of halogenated metal oxides, Lewis acid metal halides, zero-valent metals, and combinations of these, at a temperature between about 50° C. and less than 200° C.; and
   (d) withdrawing from said isomerization reactor a reaction product having a selectivity to trans-1,3,3,3-tetrafluoropropene of at least 80%.

2. The process of claim 1 wherein the metal component of said halogenated metal oxide is selected from the group consisting of: (1) transition metals having an atomic number from about 21 to about 57, (2) metals from Group IIIA having an atomic number of from about 13 to about 81, (3) metals from Group VA having an atomic number of from about 51 to about 83, (4), rare earth metals such as cerium, (5) alkali metals from Group IA having an atomic number of from about 3 to about 37, (6) alkali earth metals from Group IIA having an atomic number of from about 12 to about 56, and (7) combinations of any two or more of them.

3. The process of claim 1 wherein the metal component of said Lewis acid metal halides is selected from the group consisting of: (1) transition metals having an atomic number from about 21 to about 57, (2) metals from Group IIIA having an atomic number of from about 13 to about 81, (3) metals from Group VA having an atomic number of from about 51 to about 83, (4), rare earth metals such as cerium, (5) alkali metals from Group IA having an atomic number of from about 3 to about 37, (6) alkali earth metals from Group IIA having an atomic number of from about 12 to about 56, and (7) combinations of any two or more of them.

4. The process of claim 1 wherein when said catalyst comprises a metal from group VIII or IB, and wherein said metal is present in a form in which its oxidation state is zero.

5. The process of claim 1 wherein said feed stream introduced in accordance with step (c) comprises at least about 10% by weight of cis-1,3,3,3 tetrafluoropropene based on the total of HFO-1234ze in said feed stream.

6. The process of claim 1 wherein said feed stream introduced in accordance with step (c) comprises at least about 15% by weight of cis-1,3,3,3 tetrafluoropropene based on the total of HFO-1234ze in said feed stream.

7. The process of claim 6 wherein said feed stream further comprises un-reacted halogenated propanes.

8. The process of claim 1 wherein said converting step (a) is carried out under conditions effective to convert at least about 70% of the HFC-245.

9. The process of claim 8 wherein said reaction conditions in step (c) are effective to convert at least about 90% of the cis-HFO-1234ze.

10. The process of claim 8 wherein said reaction conditions in step (c) are effective to convert at least about 95% of the cis-HFO-1234ze and to achieve a selectivity to the trans-HFO-1234ze of at least about 98%.

11. The process of claim 1 wherein said converting step (a) comprises a liquid phase reaction.

12. The process of claim 1 wherein said converting step (a) comprises reacting said HFC-245fa with at least one material selected from the group consisting of potassium hydroxide (KOH), sodium hydroxide (NaOH), Ca(OH)2, CaO, and combinations of these.

13. The process of claim 1 wherein said converting step (a) comprises reacting said HFC-245fa with at least one dehydrofluorinating agent comprising potassium hydroxide (KOH).

14. The process of claim 13 wherein said potassium hydroxide (KOH) is present in the form an aqueous solution.

15. The process of claim 1 wherein said converting step (a) is carried out at a temperature of from about 20° C. to about 100° C.

16. The process of claim 1 wherein said converting step (a) is carried out at a temperature of from about 30° C. to about 90° C.

17. The process of claim 16 wherein the metal component of said halogenated metal oxide is selected from the group consisting of: (1) transition metals having an atomic number from about 21 to about 57, (2) metals from Group IIIA having an atomic number of from about 13 to about 81, (3) metals from Group VA having an atomic number of from about 51 to about 83, (4), rare earth metals such as cerium, (5) alkali metals from Group IA having an atomic number of from about 3 to about 37, (6) alkali earth metals from Group IIA having an atomic number of from about 12 to about 56, and (7) combinations of any two or more of them.

18. The process of claim 1 wherein the metal component of said Lewis acid metal halides is selected from the group consisting of: (1) transition metals having an atomic number from about 21 to about 57, (2) metals from Group IIIA having an atomic number of from about 13 to about 81, (3) metals from Group VA having an atomic number of from about 51 to about 83, (4), rare earth metals such as cerium, (5) alkali metals from Group IA having an atomic number of from about 3 to about 37, (6) alkali earth metals from Group IIA having an atomic number of from about 12 to about 56, and (7) combinations of any two or more of them.

19. The process of claim 1 wherein when said catalyst comprises a metal from group VIII or IB, and wherein said metal is present in a form in which its oxidation state is zero.

\* \* \* \* \*